United States Patent [19]
Suslow et al.

[11] Patent Number: 5,290,687
[45] Date of Patent: * Mar. 1, 1994

[54] CHITINASE-PRODUCING BACTERIA AND PLANTS

[75] Inventors: Trevor Suslow, El Cerrito, Calif.; Jonathan D. G. Jones, Norwich, United Kingdom

[73] Assignee: DNA Plant Technology Corporation, Mt. Kisco, N.Y.

[*] Notice: The portion of the term of this patent subsequent to Jul. 10, 2007 has been disclaimed.

[21] Appl. No.: 930,970

[22] Filed: Aug. 14, 1992

Related U.S. Application Data

[63] Continuation of Ser. No. 550,253, Jul. 9, 1990, which is a continuation-in-part of Ser. No. 888,033, Jul. 18, 1986, Pat. No. 4,940,840, which is a continuation-in-part of Ser. No. 593,691, Mar. 26, 1984, Pat. No. 4,751,081.

[51] Int. Cl.$^5$ .................... C12P 21/00; C12P 21/04; C12N 15/00; A01H 1/04
[52] U.S. Cl. .................... 435/69.1; 435/70.1; 435/172.3; 800/205
[58] Field of Search .................... 435/69.1, 70.1, 172.3; 800/205

[56] References Cited

U.S. PATENT DOCUMENTS 4,940,840  7/1990  Suslow et al. .................... 800/205

OTHER PUBLICATIONS

Goodman et al. (1987) "Gene Transfer in Crop Improvement" Science 236:48–54 (1987).
Michell and Alexander (1961) "The Mycolytic Phenomenon and Biological Control of Fusarium in Soil" Nature 190:109–110.
Sneh (1981) "Use of Rhizosphere Chitinolytic Bacteria for Biological Control" Phytopath. Z. 100:251–256.
Michael and Nelson (1972) "Antagonistic Effect of Soil Bacteria on Fusarium Roseum 'Culmorum' from Carnation" Phytopatholy 62:1052–1056.
Monteal and Reese (1969) "The Chitinase of Serratia Macescens" Canadian Journal of Microbiology 15:689–696.
Roberts and Cabib (1982) "Serratia Marcescens Chitinase: One-Step Purification and Use for the Determination of Chitin" Analytical Biochemistry 127:402–412.
Reid and Ogrydziak (1981) "Chitinase-Overproducing Mutant of Serratia Macescens" Applied and Evironmental Microbiology 41:664–669.
Kado and Lurquin (1982) "Prospectus for Genetic Engineering in Agriculture" Phytopathogenic Prokaryotes vol. 2, Mount and Lacy Eds., 303–325.
Miller and Sands (1977) "Effects of Hydrolytic Enzymes on Plant-Parasitic Nematodes" Journal of Nematology 9:192–197.
Bevan and Chilton (1982) "T-DNA of the Agrobacterium TI and RI Plasmids" Ann. Rev. Genet. 16:357–384.
Ream and Gordon (1982) "Crown Gall Disease and Prospects for Genetic Manipulation of Plants" Science 218:854–859.
Marton et al. (1979) "In Vitro Transformation of Cultured Cells from Nicotiana Tabacum by Agrobacterium Tumefaciens" Nature 27:129–131.
Horsch et al. (1984) "Inheritance of Functional Foreign Genes in Plants" Science 223:496–498.

(List continued on next page.)

Primary Examiner—David T. Fox
Attorney, Agent, or Firm—Clinton H. Neagley; William M. Smith

[57] ABSTRACT

Novel bacteria strains and plants are described which produce and secrete chitinase and other proteins as the result of the introduction of foreign DNA linked to a sequence encoding chitinase, an enzyme capable of degrading chitin present in fungi and nematodes. The bacterial strains have utility in producing chitinase for the purpose of inhibiting plant pathogens. Novel pathogen resistant plants are also described which are created by introduction of DNA encoding for the production of chitinase.

12 Claims, 6 Drawing Sheets

OTHER PUBLICATIONS

Hoekema et al. (1983) "A Binary Plant Vector Strategy Based on Separation of Vir- and T-Region of the Agrobacterium Tumefaciens TI-Plasmid" Nature 303:179-180.

Van Den Elzen et al. (1985) "Simple Binary Vectors for DNA Transfer to Plant Cells" Plant Molecular Biology 5:149-154.

Bevan (1984) "Binary Agrobacterium Vectors for Plant Transformation" Nucleic Acids Research 12:8711-8721.

Herrera-Estrella et al. (1983) "Expression of Chimaeric Genes into Plant Cells Using a TI-Plasmid-Derived Vector" Nature 303:209-213.

Fraley et al. (1983) "Expression of Bacterial Genes in Plant Cells" Proc. Natl. Acad. Sci. USA 80:4803-4807.

Odell et al. (1985) "Identification of DNA Sequences Required for Activity of the Cauliflower Mosaic Virus 35S Promoter" Nature 313:810-812.

Jones et al. (1985) "High Level Expression of Introduced Chimaeric-Genes in Regenerated Transformed Plants" The EMBO Journal 4:2411-2418.

Jones et al. (1986) "Isolation and Characterization of Genes Encoding Two Chitinase Enzymes from Serratia Macescens" The EMBO Journal 5:467-473.

Jones et al. (1986) "Engineering Bacterial Chitinase Genes for Crop Protection" Journal of Cellular Biochemistry, Supp. 10C, p. 15.

Suslow et al. 1988 Phytopathology 78 (12 Part 1): 1556.

Reeck et al. 1987 Cell 50:667.

Lewin, R. 1987 Science 237: 1570.

```
-360
CAG GGC GTT GTC AAT AAT GAC AAC ACC CTG GCT GAA GAG TGT GGT

GCA ATA CTG ATA AAT ATT TAT CTT TCC TTA ATA GAA AAT TCA CTA

-270
TCC TTA TTT GTC ATG TTT TCT TTT ATT TAT ATG AAA ATA AAT TCA

CGC TTG CTG AAT AAA ACC CAG TTG ATA GCG CTC TTG TTT TTG CGC

-180
CTT TTT TAT TTA TAG TAC TGA ATG TAC GCG GTG GGA ATG ATT ATT

TCG CCA CGT GGA AAG ACG CTG TTG TTA TTT ATT GAT TTT AAC CTT

-90
CGC GGA TTA TTG CGG AAT TTT TTC GCT TCG GCA ATG CAT CGC GAC

GAT TAA CTC TTT TAT GTT TAT CCT CTC GGA ATA AAG GAA TCA GTT

1
MET ARG LYS PHE ASN LYS PRO LEU LEU ALA LEU LEU ILE GLY SER
ATG CGC AAA TTT AAT AAA CCG CTG TTG GCG CTG TTG ATC GGC AGC

THR LEU CYS SER ALA ALA GLN ALA ALA ALA PRO GLY LYS PRO THR
ACG CTG TGT TCC GCG GCG CAG GCC GCC GCG CCG GGC AAG CCG ACC

91
ILE ALA TRP GLY ASN THR LYS PHE ALA ILE VAL GLU VAL ASP GLN
ATC GCC TGG GGC AAC ACC AAG TTC GCC ATC GTT GAA GTT GAC CAG

ALA ALA THR ALA TYR ASN ASN LEU VAL LYS VAL LYS ASN ALA ALA
GCG GCT ACC GCT TAT AAT AAT TTG GTG AAG GTA AAA AAT GCC GCC

181
ASP VAL SER VAL SER TRP ASN LEU TRP ASN GLY ASP ALA GLY THR
GAT GTT TCC GTC TCC TGG AAT TTA TGG AAT GGC GAC GCG GGC ACG

GLY PRO LYS ILE LEU LEU ASN GLY LYS GLU ALA TRP SER GLY PRO
GGA CCC AAG ATT TTA TTA AAT GGT AAA GAG GCG TGG AGT GGT CCT

-271
SER THR GLY SER SER GLY THR ALA ASN PHE LYS VAL ASN LYS GLY
TCA ACC GGA TCT TCC GGT ACG GCG AAT TTT AAA GTG AAT AAA GGC

GLY ARG TYR GLN MET GLN VAL ALA LEU CYS ASN ALA ASP GLY CYS
GGC CGT TAT CAA ATG CAG GTG GCA TTG TGC AAT GCC GAC GGC TGC

-361
THR ALA SER ASP ALA THR GLU ILE VAL VAL ALA ASP THR ASP GLY
ACC GCC AGT GAC GCC ACC GAA ATT GTG GTG GCC GAC ACC GAC GGC

SER HIS LEU PRO PRO LEU LYS GLU PRO LEU LEU GLU LYS ASN LYS
AGC CAT TTG CCG CCG TTG AAA GAG CCG CTG CTG GAA AAG AAT AAA
```

*FIG. 1A.*

```
451
PRO TYR LYS GLN ASN SER GLY LYS VAL VAL GLY SER TYR PHE VAL
CCG TAT AAA CAG AAC TCC GGC AAA GTG GTC GGT TCT TAT TTC GTC

GLU TRP GLY VAL TYR GLY ARG ASN PHE THR VAL ASP LYS ILE PRO
GAG TGG GGC GTT TAC GGG CGC AAT TTC ACC GTC GAC AAG ATC CCG

541
ALA GLN ASN LEU THR HIS LEU LEU TYR GLY PHE ILE PRO ILE CYS
GCG CAA AAC CTG ACC CAC CTG CTG TAC GGC TTT ATC CCG ATC TGC

GLY GLY ASN GLY ILE ASN ASP SER LEU LYS GLU ILE GLU GLY SER
GGC GGC AAT GGC ATC AAC GAC AGC CTG AAA GAG ATT GAA GGC AGC

631
PHE GLN ALA LEU GLN ARG SER CYS GLN GLY ARG GLU ASP PHE LYS
TTC CAG GCG TTG CAG CGC TCC TGC CAA GGC CGC GAG GAC TTC AAA

ILE SER ILE HIS ASP PRO PHE ALA ALA LEU GLN LYS ALA GLN LYS
ATC TCG ATC CAC GAT CCG TTC GCC GCG CTG CAA AAG GCG CAG AAG

721
GLY VAL THR ALA TRP ASP ASP PRO TYR LYS GLY ASN PHE GLY GLN
GGC GTG ACC GCC TGG GAT GAC CCC TAC AAG GGC AAC TTC GGC CAG

LEU MET ALA LEU LYS GLN ALA HIS PRO ASP LEU LYS ILE LEU PRO
CTG ATG GCG CTG AAG CAG GCG CAT CCT GAC CTG AAA ATC CTG CCG

811
SER ILE GLY GLY TRP THR LEU SER ASP PRO PHE PHE PHE MET GLY
TCG ATC GGC GGC TGG ACG CTG TCC GAC CCG TTC TTC TTC ATG GGC

ASP LYS VAL LYS ARG ASP ARG PHE VAL GLY SER VAL LYS GLU PHE
GAC AAG GTG AAG CGC GAT CGC TTC GTC GGT TCG GTG AAA GAG TTC

901
LEU GLN THR TRP LYS PHE PHE ASP GLY VAL ASP ILE ASP TRP GLU
CTG CAG ACC TGG AAG TTC TTC GAC GGC GTG GAT ATC GAC TGG GAG

PHE PRO GLY GLY LYS GLY ALA ASN PRO ASN LEU GLY SER PRO GLN
TTC CCG GGC GGC AAA GGC GCC AAC CCT AAC CTG GGC AGC CCG CAA

991
ASP GLY GLU THR TYR VAL LEU LEU MET LYS GLU LEU ARG ALA MET
GAC GGG GAA ACC TAT GTG CTG CTG ATG AAG GAG CTG CGG GCG ATG

LEU ASP GLN LEU SER ALA GLU THR GLY ARG LYS TYR GLU LEU THR
CTG GAT CAG CTG TCG GCG GAA ACC GGC CGC AAG TAT GAG CTG ACC

1081
SER ALA ILE SER ALA GLY LYS ASP LYS ILE ASP LYS VAL ALA TYR
TCC GCC ATC AGC GCC GGT AAG GAC AAG ATC GAC AAG GTG GCT TAC

ASN VAL ALA GLN ASN SER MET ASP HIS ILE PHE LEU MET SER TYR
AAC GTT GCG CAG AAC TCG ATG GAT CAC ATC TTC CTG ATG AGC TAC
```

FIG. 1B.

```
1171
ASP PHE TYR GLY ALA PHE ASP LEU LYS ASN LEU GLY HIS GLN THR
GAC TTC TAT GGC GCC TTC GAT CTG AAG AAC CTG GGG CAT CAG ACC

ALA LEU ASN ALA ARG PRO GLY SER ARG HIS ARG LEU HIS HIS GLY
GCG CTG AAT GCG CGG CCT GGA AGC CGA CAC CGC TTA CAC CAC GGT

1261
GLU ARG ARG GLU CYS ALA ALA GLY GLN GLY VAL LYS PRO GLY LYS
GAA CGG CGT GAA TGC GCT GCT GGC CAG GGC GTC AAG CCG GGC AAA

ILE VAL VAL GLY THR ALA MET TYR GLY ARG GLY TRP THR GLY VAL
ATC GTC GTC GGC ACC GCC ATG TAT GGC CGC GGC TGG ACC GGG GTG

1351
ASN GLY TYR GLN ASN ASN ILE PRO PHE THR GLY THR HIS ARG ALA
AAC GGC TAC CAG AAC AAC ATT CCG TTC ACC GGC ACG CAC CGG GCC

VAL LYS GLY THR TRP GLU ASN GLY ILE VAL ASP TYR ARG GLN ILE
GTT AAA GGC ACC TGG GAG AAC GGC ATC GTG GAC TAC CGC CAA ATC

1441
ALA SER GLN PHE MET SER GLY GLU TRP GLN TYR THR TYR ASP ALA
GCC AGC CAG TTC ATG AGC GGC GAG TGG CAG TAT ACC TAC GAC GCC

THR ALA GLU ALA PRO TYR VAL PHE LYS PRO SER THR GLY ASP LEU
ACG GCG GAG GCG CCT TAC GTG TTC AAA CCT TCC ACC GGC GAT CTG

1531
ILE THR PHE ASP ASP ALA ARG SER VAL GLY ALA LYS GLY LYS TYR
ATC ACC TCC GAC GAT GCC CGC TCG GTG CAG GCT AAA GGC AAG TAC

VAL LEU ASP LYS GLN LEU GLY GLY LEU PHE SER TRP GLU ILE ASP
GTG CTG GAT AAA CAG CTG GGC GGC CTG TTC TCC TGG GAG ATC GAC

1621
ALA ASP ASN GLY ASP ILE LEU ASN SER MET ASN ALA SER LEU GLY
GCG GAC AAC GGC GAT ATT CTC AAC AGC ATG AAC GCC AGC CTG GGC

ASN SER ALA GLY VAL GLN ***
AAC AGC GCC GGC GTT CAA TAA TCG GTT GCA GTG GTT GCC GGG GGA

1711
TAT CCT TTC GCC CCC GGC TTT TTC GCC GAC GAA AGT TTT TTT ACG

CCG CAC AGA TTG TGG CTC TGC CCC GAG CAA AAC GCG GTC ATC GGA

1801
CTC ACC CTT TTG GGT AAT CCT TCA GCA TTT CCT CCT GTC TTT AAC

GGC GAT CAC AAA AAT AAC CGT TCA GAT AAT CAT CAT TCA GCA ACA

1891
AAG TTT TGG CGT TTT TTA ACG GAG TTA AAA ACC AGT AAG TTT GTG

AGG GTC AGA CCA ATG CGC TAA AAA TGG G
```

*FIG. IC.*

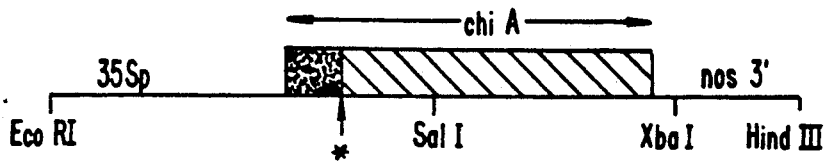
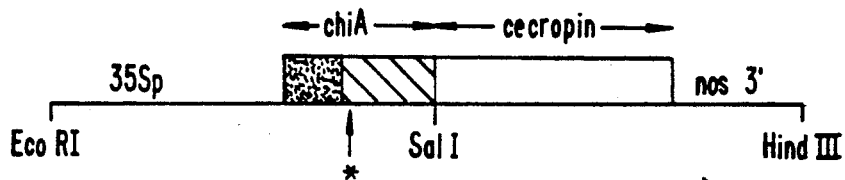
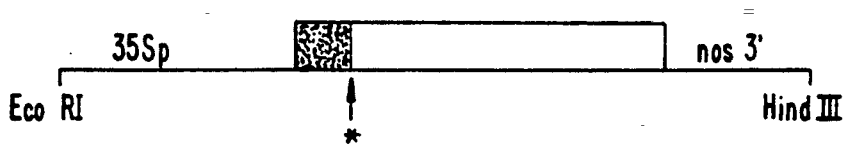
FIG. 3.

| ATG | CGC | AAA | TTT | AAT | AAA | CCG | CTG | TTG | GCG | CTG |
| --- | --- | --- | --- | --- | --- | --- | --- | --- | --- | --- |
| TTG | ATC | GGC | AGC | ACG | CTG | TGT | TCC | GCG | GCG | CAG |
| GCC | * | AAA | TGG | AAG | CTT | TTC | AAA | AAA | ATC | GAA |
| AAA | GTT | GGT | CAG | AAC | ATC | CGT | GAC | GGT | ATC | ATC |
| AAA | GCT | GGT | CCG | GCT | GTT | GCT | GCT | GTT | GTT | GGT |
| CAG | GCT | ACC | CAG | ATC | GCT | AAA | TAA | | | |

* INDICATES THE JUNCTION BETWEEN THE chiA SIGNAL AND THE CECROPIN A CODING REGION.

*FIG. 4.*

CHITINASE-PRODUCING BACTERIA AND PLANTS

This invention was made with Government support under Grant No. 1S1-8560311 awarded by the National Science Foundation. The Government has certain rights in this invention.

This application is a continuation of pending U.S. application Ser. No. 07/550,253, filed Jul. 9, 1990, which is a continuation-in-part of U.S. Ser. No. 06/888,033, filed Jul. 18, 1986, which issued as U.S. Pat. No. 4,940,840, which is a continuation-in-part of U.S. Ser. No. 06/593,691, filed Mar. 26, 1984, which issued as U.S. Pat. No. 4,751,081, all in the names of Trevor V. Suslow and Jonathan D. G. Jones, all of which are incorporated herein by reference.

This invention relates to novel man-made bacterial strains which produce chitinase, an enzyme which degrades chitin. This invention further relates to the use of such strains as a means to inhibit soil fungi and nematodes and to enhance plant growth by biological control of plant pathogens. This invention additionally relates to the introduction of chitinase activity into plants and to plants which have been rendered resistant to plant pathogens as a result of such introduction. Finally, this invention relates to the introduction into plant cells of a sequence from the chitinase gene that directs the secretion of polypeptides encoded by foreign DNA.

The soil contains a wide variety of life forms which can interact with plants, including bacteria, fungi and nematodes. These life forms are especially abundant in the rhizosphere, the area of the soil that surrounds and is influenced by the plant roots. As used herein the term rhizosphere embraces the rhizoplane, the root-soil interface including the surface of the root. The term rhizobacteria, as used herein, refers to bacteria adapted to the rhizosphere. The interactions between these soil inhabiting life forms are complex, some being antagonistic and others being mutually beneficial.

The interactions between plants and the various soil life forms are similarly complex, in some instances helpful to the plant and in other instances deleterious to the plant. Fungi harmful to plants (fungal pathogens) include fungal species from a wide variety of genera, including Fusarium, Pythium, Phytophthora, Verticillium, Rhizoctonia, Macrophomina, Thielaviopsis, Sclerotinia and numerous others. Plant diseases caused by fungi include pre and post-emergence seedling damping-off, hypocotyl rots, root rots, crown rots, vascular wilts and a variety of other forms of symptom development. Nematodes harmful to plants (nematode pathogens) include nematode species from the genera Meloidogyne, Heterodera, Ditylenchus, Pratylenchus. Plant diseases caused by nematodes include root galls, root rot, lesions, "stubby" root, stunting, and various other rots and wilts associated with increased infection by pathogenic fungi. Some nematodes (e.g., Trichodorus, Lonaidorus, Xiphenema) can serve as vectors for virus diseases in a number of plants including Prunus, grape, tobacco and tomato.

Various approaches are available for attempting to control deleterious fungi and nematodes. One method, long known in the art, is chemical treatment of soil or plants with fungicides or nematicides. Another method is application of certain naturally occurring bacteria which inhibit or interfere with fungi or nematodes. See, in general, K. F. Baker and R. J. Cook, *Biological Control of Plant Pathogens*, Freeman and Co. (1974) for a description of fungi and nematodes and their interaction with plants, as well as a description of means for biological control of fungal and nematode pathogens.

One approach to biocontrol of fungal and nematode pathogens is based on the widespread presence of chitin as an integral part of the cell walls of fungi and the outer covering of nematodes or nematode eggs or nematode cysts. Chitin is an unbranched polysaccharide polymer consisting of N-acetyl-D-glycocyamine units. It is insoluble in water, dilute mineral acids and bases but can be broken down enzymatically by chitinase, the degradation products being soluble monomers or multimers of N-acetyl-D-glycocyamine. Chitinase is produced by certain naturally occurring bacteria and fungi and there have been reports of the role of chitinase in the suppression of pathogens.

R. Mitchell and M. Alexander, "The Mucolytic Phenomenon and Biological Control of Fusarium in Soil", *Nature*, 190, 109–110 (1961) describes naturally occurring mucolytic, or fungi-lysing, soil bacteria (genera Bacillus and Pseudomonas) which suppress soil Fusarium by means of chitinase activity. B. Sneh, "Use of Rhizosphere Chitinolytic Bacteria for Biological Control", *Phytopath. Z.*, 100, 251–56 (1981) discloses naturally occurring chitinolytic isolates identified as *Arthrobacter sp.* and *Serratia liquifaciens*. Sneh also discloses introduction of a chitinolytic bacterial strain from the genus Arthrobacter into the rhizosphere to protect carnation seedlings from Fusarium wilt A. H. Michael and P. E. Nelson, "Antagonistic effect of soil bacteria on *Fusarium roseum culmorun*", Phytopathology, 62, 1052–1056 (1972) discloses similar control with a naturally occurring Pseudomonas species.

J. Monreal and E. T. Reese, "The Chitinase of *Serratia marcescens*", *Canadian Journal of Microbiology*, 15, 689–696 (1969) describes a Serratia marcescens bacterial strain (QMB1466) selected as the most active chitinase producer out of a number of naturally occurring bacterial and fungal strains tested. Other strains tested which displayed some chitinase activity included bacterial strains from the genera Enterobacter and Streptomyces, and fungal strains from the genera *Aspergillus, Penicillium* and Trichoderma. Chitinase is characterized as an induced enzyme system in strain QMB1466, i.e., the yields of chitinase produced by the strain were higher when chitin was present. Monreal et al. reports at p. 692 that chitinase production on a chitin medium is repressed by the addition of other carbon-containing metabolites, e.g., sugars, to the medium. The *Serratia marcescens* enzyme system is described as extracellular and including endochitinase, a chitobiase and a "factor" for hydrolysis of "crystalline" chitin.

The naturally occurring Serratia marcescens chitinase system is further described in R. L. Roberts and E. Cabib, "*Serratia Marcescens* Chitinase: One-Step Purification and Use for the Determination of Chitin", *Analytical Biochemistry*, 127, 402–412 (1982).

J. D. Reid and D. M. Ogrydziak, "Chitinase-Overproducing Mutant of *Serratia marcescens*", *Applied and Environmental Microbiology*, 41, 664–669 (1981) describes work with a mutant of *Serratia marcescens*, strain IMR-1E1, obtained by mutation of strain QMB1466. The mutant had increased chitinase activity compared to strain QMB1466, as measured by zones of clearing on chitin-agar plates. On page 664 Reid et al. refers to the "high rate of reversion of IMR-1E1 to decreased levels of chitinase production."

C. I. Kado and P. F. Lurguin, "Prospectus for Genetic Engineering in Agriculture", *Phytopathogenic Prokaryotes*, Vol. 2, M. S. Mount and G. H. Lacy eds., 309 (1982), while not discussing the role of chitinase in controlling chitin-containing pathogens, notes the possibility of a different approach to controlling fungi, namely, inserting into bacteria genes coding for compounds which inhibit chitin synthase in fungi. That is, the compound chitin synthase, necessary for production of chitin in fungi, would be inhibited by the bacterial compounds.

P. M. Miller and D. C. Sands, "Effects of Hydrolytic Enzymes on Plant-parasitic Nematodes", *Journal of Nematology*, 9, 192–197 (1977) describes the effect of chitinase, obtained from a commercial supplier, on certain nematodes. Miller et al. discloses that chitinase hydrolytic enzymes are toxic to certain nematodes, in particular *Tylenchorhynchus dubius*, the toxicity being greater in aqueous solution than in soil.

There are a number of limiting factors and disadvantages with respect to work to date on biological control of plant pathogens using chitinase-producing bacteria introduced into the soil. First is the inability to regulate the production of chitinase in the introduced bacteria in such a way that proper amounts of chitinase are produced Second is the limited ability of many of such bacteria to colonize and persist in the rhizosphere of host plants, a key consideration for effective biocontrol. Particularly important in this respect is the ability of biocontrol bacteria to colonize the roots of host plants effectively, the roots being the site of much plant-pathogen interaction. Third is that chitinase production is repressed in the presence of other carbon sources, e.g., metabolites released by the root. Another problem, at least as to mutants, is reversion to forms exhibiting decreased levels of chitinase production. There have been a number of reports of methods for introducing foreign DNA into plants. One approach is introduction by transformation using Agrobacterium, in particular *Agrobacterium tumefaciens*; M. Bevan et al., *Ann. Rev. Genet.*, 16, 357–384 (1982); L. Ream et al., *Science*, 218, 854–859 (1982). This introduction may be carried out by cocultivation of plant protoplasts with Agrobacterium, followed by plant regeneration; Marton et al., *Nature*, 277, 129–131 (1979); R. B. Horsch et al., *Science*, 223, 496–498 (1984). The introduction may also be carried out using binary vectors; A. Hoekema et al., *Nature*, 303, 179–180 (1983); P. van den Elzen et al., *Plant Mol. Biol.*, 5, 149–154 (1985); M. Bevan, *Nucl. Acids Res.*, 12, 8711–8721 (1984). Where the foreign DNA is from a non-plant source, the foreign DNA (structural gene, i.e., encoding sequence) may be fused to a plant promoter; L. Herrera-Estrella et al. *Nature*, 303, 209–213 (1983); R. T. Fraley et al., *Proc. Natl. Acad. Sci.* 80, 4803–4807 (1983); J. T. Odell et al., *Nature*, 313, 810–812 (1985); J. Jones et al., *EMBO J.*, 4, 2411–2418 (1985).

SUMMARY OF THE INVENTION

The present invention provides novel plant cells comprising a DNA sequence from a gene encoding chitinase A that directs secretion of a foreign polypeptide from the plant cell. The DNA sequence can be introduced into the plant cell using techniques well known in the art for transforming plant cells. Preferably, Agrobacterium is used to introduce the DNA into the plant cell. To obtain expression of the DNA sequence, plant expression control sequences are typically fused to the gene. The petunia ribulose bisphposphate small subunit promoter, the chlorophyll A/B binding protein promoter, and the nopaline synthase promoter are among the suitable promoters.

Plants transformable by methods known in the art can be used in the present invention. For example, when tobacco plants are used, the transformants secrete an exogenous polypeptide encoded by foreign DNA, such as biologically active chitinase A. The invention further provides recombinant plasmids comprising a DNA sequence from a gene encoding chitinase A that directs secretion by a plant cell of the polypeptide encoded by foreign DNA.

BRIEF DESCRIPTION OF THE DRAWINGS

FIGS. 1A–1C are the DNA sequence of a 2.3 kb DNA fragment from pCHIT1251, as determined by M13-dideoxyuucleotide DNA sequencing. The predicted amino acid sequence of the chitinase A gene is given above the nucleotide sequence.

FIG. 3 shows the construction of CEC 3, the plasmid carrying the fusion of cecropin A gene to the sequence encoding the chitinase A signal sequence.

FIG. 4 is the sequence of the fragment encoding the fusion of the cecropin A gene and the sequence encoding chitinase A signal sequence.

DESCRIPTION OF THE PREFERRED EMBODIMENTS

Figure 2:
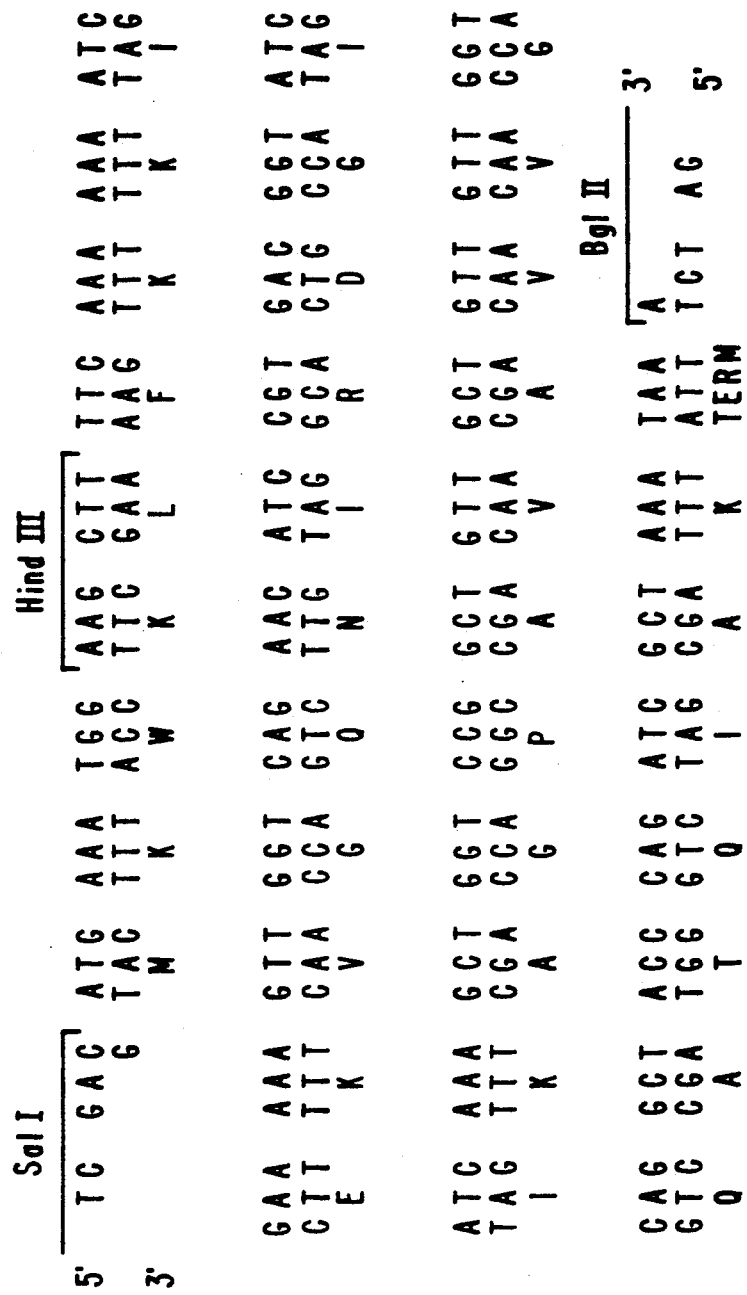
FIG. 2 is the DNA sequence of a fragment which encodes the mature cecropin A peptide flanked by Sal I and Bgl II restriction sites.

The present invention comprises novel man-made bacteria and plants, which have the ability to produce and secrete chitinase and other proteins as the result of introduction of foreign DNA. The foreign DNA is isolated from a foreign source, bacterial or otherwise, or is substantially homologous to such DNA.

The term "substantial homology" refers to nucleotide sequences which share a majority of their sequence. Generally, this will be at least about 90% of their sequences and preferably about 95% of their sequence. Another indication that sequences are substantially homologous is if they hybridize under stringent conditions (see, e.g., Maniatis et al., *Molecular Cloning—A Laboratory Manual*, Cold Spring Harbor Laboratory, Cold Spring Harbor, N.Y., 1982. Stringent conditions will depend upon various parameters and will be different in different circumstances. Generally, stringent conditions are those in which the salt concentration is at least about 0.2 molar and the temperature is at least about 60° C.

The novel bacteria can be prepared using various means, including the use of appropriate vectors, for introducing the foreign DNA, and thus the capacity to produce chitinase, into a bacterial cell or a parent of a bacterial cell under conditions where chitinase activity is expressed. The vectors are used to clone and introduce the foreign DNA which encodes for chitinase activity. The novel bacteria can be used to introduce chitinase into the soil, particularly into the soil rhizosphere, thereby providing a means of inhibiting chitin-containing or chitinase-sensitive plant pathogens, including fungi and nematodes, and thereby also providing a means of enhancing the growth and well being of plants sensitive to such pathogens.

The present invention provides a means of overcoming limitations of the prior art methods of bacterial control of chitinase-sensitive plant pathogens. The invention provides a means of introducing sufficient chitinase production capacity into a strain. The invention also provides a means to introduce chitinase capacity into strains best suited to function in the soil and rhizosphere, in particular root colonizing rhizobacteria strains. Further, in accordance with the invention, the problem of reversion of modified strains to wild type is overcome in that the novel strains of the invention result from the actual introduction of genetic material, rather than from mutation. Additionally, the invention provides the means to overcome the problem of repression of chitinase activity in the presence of root exudates or other carbon sources, in that regulatory systems can be employed which render the bacterial cell insensitive to such repression.

The present invention further comprises a method of introducing into plants the ability to produce chitinase as the result of introduction into the plant of foreign DNA encoding for chitinase activity Accordingly, the invention also comprises a method of inhibiting chitinous (chitin containing) plant pathogens by such introduction of foreign DNA under conditions whereby the plant produces (expresses) chitinase in active form. More particularly, plants may be protected against fungi, nematodes, insects and disease agents. As used herein, "in active form" means chemically active (capable of degrading chitin) or biologically active (capable of inhibiting chitinous plant pathogens). In addition, portions of the chitinase A gene encoding the signal sequence (i.e. the leader peptide that allows the protein to be secreted) can be linked to foreign DNA other than the chitinase A gene.

The foreign DNA to be introduced into the plant is isolated from a foreign source, in particular a bacterial source, or is substantially homologous to such DNA. The foreign DNA is introduced into the plant using plant transformation techniques, in particular using Agrobacterium procedures whereby the foreign chitinase DNA is first introduced into Agrobacterium in an appropriate vector, in accordance with the method of the invention, and then introduced into the plant by transformation with Agrobacterium. Such introduction into the plant is preferably carried out where the foreign DNA is fused to a plant promoter such that the foreign DNA (the structural gene) is under the transcriptional control of the plant promoter. Preferred sources of foreign chitinase DNA for plant transformation are ATCC accession numbers 39637 and ATCC 67152.

The present invention in addition comprises plants which have been rendered resistant to, or capable of inhibiting, chitinous plant pathogens by virtue of introduction of foreign chitinase encoding DNA into the plant under conditions whereby the transformed plant expresses chitinase in active form. The invention also comprises progeny of such transformed plants. As used herein "transformed plant" means a plant into which foreign DNA has been introduced. Any transformable plant may be transformed in accordance with the invention. The term "plant" as used herein includes whole plants, plant parts, seeds, plant cells, plant calli and plant tissue cultures. Preferred plants for transformation in accordance with the invention include tobacco, Brassica spp., soybean, sugarbeet, cotton, tomato, pepper, alfalfa, potato, wheat, barley, rice and corn.

The novel bacterial cells of the invention are made by introduction of foreign DNA, or heterologous DNA, which codes for production of, or expression of, the enzyme chitinase. The term "chitinase" is used herein to mean chitin-degrading enzyme, the term "chitin-degrading" embracing both chitin-hydrolyzing and chitin-solubilizing. The term "chitinase DNA" is used herein to mean DNA which encodes for chitinase, and embraces foreign chitinase DNA obtained directly or indirectly from a source organism, including bacteria, fungi and plants, as well as DNA which regardless of source is substantially homologous to such foreign chitinase DNA. "Chitinase activity", or "chitinolytic activity", as used herein, means the ability or capacity of a bacterial cell to produce chitinase. Such chitinase can be secreted by the bacteria into the immediate environment.

Chitinase DNA can be obtained from a wide variety of naturally occurring bacteria which are known to or can be shown to produce chitinase, including bacteria from the genera Serratia, Bacillus, Pseudomonas, Arthrobacter, Enterobacter, and Streptomyces. Bacterial strains containing chitinase DNA have been known and available from laboratories or collections for years. For instance, chitinase-producing *Serratia marcescens* strain QMB1466, which was described by Monreal et al. in 1969 and by Reid et al. in 1981, (in each case the reported source of the strain being the U.S Army Natick Laboratory Culture Collection) is available from a number of sources, including the American Type Culture Collection at Rockville, Md. (ATCC 990). Chitinase-containing bacterial strains are also readily obtainable by known techniques by virtue of their widespread distribution in nature. Such strains in general are found in soil, on plants, on insects and in water systems, as well as in other places where chitin is present. For example, chitinolytic bacteria can be isolated from the rhizosphere of a wide variety of plants including sugar beet, cotton, bean or carnation. Chitinase-producing bacteria can also be obtained from root surfaces, fungal resting structures (e.g., sclerotia, chlamydospores), nematode egg masses, insect or arthropod exo-skeleton and irrigation water.

Isolation of bacterial strains containing chitinase DNA can be accomplished by a number of techniques, including direct isolation on chitin containing media, enrichment or baiting with chitin or fungal hyphae. These techniques are common and known to those skilled in the art. Chitinase-producing fungi can be isolated from sources such as those stated above for chitinolytic bacteria, again using standard techniques for plating fungi. See, in general, J. Tuite, *Plant Pathological Methods: Funqi and Bacteria*, Burgess Publishing Co. (1969) with respect to techniques for isolation of bacteria and fungi.

Foreign chitinase DNA for conferring chitinase activity on a host or recipient bacterium can be obtained directly from a source organism, e.g., bacteria, fungi, yeast, insect or plant, using techniques of genome fragmentation and DNA isolation known to those skilled in the art. For instance, for a bacterial source organism, isolated as explained above, total bacterial DNA (that is, the entire genome including chromosomal DNA and extra-chromosomal DNA) is isolated by standard techniques, e.g., lysis of bacteria in the presence of appropriate detergents, proteases and chelating agents, followed by phenol and chloroform extractions and precipitation with ethanol. The isolated DNA is partially digested to various degrees with an appropriate restriction enzyme or enzymes selected on the basis of appropriate sites in the cloning vector which is to be used. The products of the digestion process are fractionated by standard techniques, for instance on a glycerol gradient. Fractions containing DNA in an appropriate size range, e.g., about 22 to about 32 kb (kilo bases), are selected for insertion into an appropriate vector using known techniques, for instance as described below, thus yielding a genomic library (consisting of cosmid clones, in the case of a cosmid vector).

An alternative to obtaining chitinase DNA directly by genome fragmentation of a source organism is obtaining chitinase DNA indirectly by isolating, from the source organism, messenger RNA (mRNA) corresponding to chitinase DNA. A cDNA (copy DNA) library can be prepared from the mRNA, using reverse transcriptase in accordance with techniques known to those skilled in the art, and inserted into an appropriate cDNA expression vector, such that clones encoding chitinase activity could be detected by clearing of chitin on plates.

The choice of particular vector turns on a number of considerations known to those skilled in the art, including the size of the fragment, nature of the host, number and position of restriction sites desired, and selection marker or markers desired. Techniques for introduction of DNA into a vector and subsequent introduction of the vector into the host bacteria are known to those skilled in the art. See in general T. Maniatis et al, "Molecular Cloning, a Laboratory Manual," Cold Spring Harbor Publications, 1982 (hereinafter Maniatis) with respect to techniques for insertion of DNA fragments into a host bacterium (as well as with respect to general techniques for fragmentation and fractionation of a genome.)

Introduction of foreign DNA into the host bacteria results in the creation of a bank of modified (i.e. transformed or transduced) host bacteria which can be screened for chitinase DNA. In many cases the host bacteria will be *E. coli*. The screening can be carried out by plating the host strains on a medium which contains chitin, e.g., colloidal chitin. The development of zones of clearing in the chitin around a colony is evidence that the colony is chitinolytic. Microscopic examination showing dissolution of surrounding chitin particles is further evidence. Alternative means to screen will be apparent to those skilled, e.g., plating on a fungal lawn, or chemical tests to show the presence of chitinase.

For those bacteria shown by screening to exhibit chitinase activity, there can be optionally employed a subsequent subcloning to reduce the quantity of cloned DNA which is not involved in the coding for chitinase. An appropriate enzyme digestion is carried out and the digestion products ligated to another more convenient cloning vector, e.g., one with high copy number, and the ligation products are again transformed into *E. coli* bacteria by known techniques. Transformants are screened for chitinase production as described above.

After the cloning and any subcloning, if desired, the chitinase DNA can be transferred from the first host (transferor or donor) bacterial cell into a second host (transferee or recipient) bacterial cell. This transfer can be accomplished using known techniques, for instance by conjugation using helper plasmids to mobilize the plasmid into the transconjugant cell, the specifics depending on the transferor bacterium, the recipient bacterium, and the cloning vector which is used to propagate the chitinase DNA. For instance, if the chitinase DNA is cloned on an IncP (incompatibility group P) type plasmid derivative, such as pLAFR1, transfer to a second host strain in many instances can be accomplished by conjugation, e.g., using a helper plasmid such as pRK2013. See in general G. Ditta et al, "Broad Host Range DNA cloning system for Gram-negative bacteria: Construction of a gene bank of *Rhizobium meliloti*, Proc. Acad. Sci., 77, 7347–7351 (1980) (hereinafter Ditta), with respect to conjugation using helper plasmids Where the intended use of the bacteria modified to have chitinase ability is in control of plant pathogens residing in the soil, the bacteria of choice will normally be rhizobacteria. In that event chitinase DNA is transferred from the first host, normally *E. coli*, into the second host rhizobacterial strain.

Depending on the systems and circumstances involved in transferring a vector containing chitinase DNA from one bacterial cell to another, various techniques known to those skilled in the art may be used to ensure proper expression of the chitinase DNA in the host. For instance, an effective regulatory or promoter system will be necessary to bring about proper expression, that is, to ensure that the production of chitinase, encoded for by foreign chitinase DNA, can be brought about under conditions where chitinase production is desired If the promoter from the source organism (i.e, the promoter which normally works in the source organism with the foreign chitinase DNA) is not effective in the host, it may be necessary to incorporate into the vector a regulatory system different from that which controlled the foreign DNA in the source organism. A promoter system of choice may be one which allows the bacterial cell to produce chitinase in a manner insensitive to the presence of carbon sources, e.g., root metabolites, in the immediate environment.

That is, the cell can be made to produce chitinase constitutively. Various other techniques to enhance chitinase activity in the modified cell may be employed as well, e.g., multicopy vectors or means to enhance secretion of the chitinase from the cell.

Plasmids containing chitinase DNA, i.e., clones or chimeric plasmids, can be introduced into a bacterial host by transformation, e.g., using $CaCl_2$, the transformed cell being called the transformant. The plasmid may be a cosmid vector containing chitinase DNA, i.e., a cosmid clone, and if so it can also be introduced into the bacterial cell by transduction, the product cell being the transductant.

The particular adaption of rhizobacterial cells to the rhizosphere is related to their ability to multiply and compete at the root-soil interface or the root surface, or in the intercortical cell spaces. Root colonizing rhizobacteria typically reach population densities of $10^4$ or greater colony forming units (cfu) per mg of root tissue, from low initial populations, during the first several weeks of plant growth. Various rhizobacteria have been described, including strains from the genera Pseudomonas (in particular *P. fluorescens* and *P. nutida*), Agrobacterium, Enterobacter and Alcaliaenes. See inn general T. Suslow, "Role of Root-Colonizing Bacteria in Plant Growth", *Phytopathogenic Prokaryotes*, Vol. 1, M. S. Mount and G. H. Lacy eds, 187–223 (1982) for a discussion of root colonizing rhizosphere bacteria and their properties The choice of root colonizing strain to receive chitinase DNA will turn on the plant to be protected, the pathogen or pathogens to be protected against, the method of application, and the cultural practices related to the crop of interest For bacterial strains which already have some chitinase activity, introduction of chitinase DNA in accordance with the present invention serves to enhance chitinase activity in the host. Other bacteria already have anti-fungal (fungicidal) or anti-nematodal (nematicidal) capacity by some mechanism other than chitinase activity, in which case introduction of chitinase DNA confers chitinase activity and enhances anti-pathogen ability The present invention can also be used in combination with the introduction of some other foreign DNA, that is foreign DNA other than chitinase DNA, into a bacteria or plant. For instance, in the case of rhizobacteria, such other foreign DNA could provide the host with some other form of anti-pathogen activity or with some other means to allow it to enhance the soil environment to the benefit of the plant. Another example is the introduction into a plant cell of a foreign gene attached to the nucleotide sequence encoding the signal peptide sequence of the chitinase A gene. Such foreign genes for introduction into a plant cell could be from a variety of sources (e.g., bacterial, plant, mammalian, yeast or fungal) and from a number of classes of genes, e.g., genes to protect plants against pathogens (including antifungal genes, e.g., cecropin, magainin, attacins or lysozymes); genes to protect plants against environmental stresses (such as antifreeze genes and salt tolerance genes); and genes to allow plant cells to produce desired pharmaceutical or other peptides, in particular where the peptide is to be overproduced for collection and purification (such as genes for growth hormones or insulin). The expressed polypeptide will then be released into the environment.

The present invention is of agricultural use as a means for the production of chitinase, including the production of chitinase as an antibiotic for the purpose of degrading or otherwise inhibiting, repelling or killing plant pathogens harmful to a wide variety of agricultural crops.

The invention has particular utility for inhibiting chitinase-sensitive fungi or nematodes (that is, fungi or nematodes which are inhibited, repelled or destroyed in the presence of chitinase), where such fungi or nematodes or their activities in soil or on plant surfaces are harmful to plants. Regardless of the mechanism by which such pathogens are injurious to plants, their inhibition serves to enhance plant growth and health.

Bacteria, and particularly rhizobacteria, modified in accordance with the present invention and grown to sufficient proportions, e.g., by fermentation, can be used to combat chitin-containing soil pathogens by application of the bacteria to soil, seeds, vegetative plant parts or irrigation water. For example, mucolytic bacteria created in accordance with the invention can be used in such ways to attack or inhibit fungi. The modified bacteria can be applied in various formulations containing agronomically acceptable adjuvants or carriers in dosages and concentrations chosen to maximize the beneficial effect of the rhizobacteria.

For application to soil, to soil mixes, or to artificial plant growth media, the modified bacteria may be applied as a powder or granule in a suitable carrier. Alternatively, the modified bacteria may be applied as a suspension or dispersion, e.g., as an aqueous suspension with a suitable protectant such as methylcellulose, dextran, dextrin, alginate, magnesium silicate. The modified bacteria may also be applied as a wettable powder.

For application to seeds, the modified bacteria may be applied as part of a seed coating composition, for instance mixed with xanthan gum, magnesium silicate, methylcellulose, gum arabic, polyvinyl pyrollidone, dextrins or dextrans. In addition, small amounts of partially hydrolyzed chitin may be added to the pelleting mix, dust granule, suspension, or wettable powder to enhance chitinase production. See in general T. Suslow et al., "Rhizobacteria of sugar beets: effects of seed application and root colonization on yield", *Phytopathology*, 72, 199–206 (1982); and, J. Kloepper et al., "Development of a powder formulation for inoculation of potato seed pieces", *Phytopathology*, 71, 590–592 (1981), for a discussion of rhizobacteria and seed coating compositions, both of which are incorporated herein by reference.

Bacteria into which chitinase capability has been introduced by this invention may also be applied to the above-ground surface of a plant, e.g., the leaf or stem surface, either to permit the modified bacteria to travel or spread to the roots or to inhibit chitinase-sensitive pathogens which may be present on blossoms or plant surfaces, for instance, fungal pathogens such as Botrytis, Monilinia, Alternaria, and Cercospora. Blossoms of Prunus sp., in particular, provide an ideal environment for the growth of epiphytic bacteria, e.g., *Pseudomonas syringae* or *Erwinia herbicola*, that have the ability to produce inhibitory levels of chitinase. Similar results can be obtained by introducing chitinase-producing capacity directly into the plant.

The method of the invention can also be used for introduction of chitinase genes into species of Rhizobium which enter into a nitrogen fixing symbiosis within the nodules of leguminous plants. The nodules are frequently the point of entry of pathogenic fungi and nematodes.

The method of the invention additionally provides a means to introduce chitinase DNA into a bacterium, e.g., Agrobacterium, which is used to transfer the foreign DNA to plants. Other known means of transforming plants are also available to transfer chitinase or other foreign DNA to plants and the invention is not limited to any given method of transformation. Such transfer results in a direct means for the plant to inhibit chitinase-sensitive plant pathogens, either alone or in conjunction with bacteria modified to have chitinase ability. A particularly attractive form of such transfer is one where the chitinase DNA is expressed by the plant only at the site of pathogen attack, e.g., only in the root cells.

Both of the above applications (introduction of chitinase activity into Rhizobium or plants) would involve subcloning the chitinase genes and bringing them under the control of different regulatory sequences from those which act in the source organism. For example, elevated expression in *E. coli* could be brought about by using the lac z system (B-galactosidase structural gene promoter). In nodules elicited by Rhizobium a nitrogenase promoter could be used, and in plant leaves the promoter of a highly expressed leaf gene could be used. Any of a number of such plant promoters can be used in accordance with the invention. As used herein, the term "plant promoter" means a promoter, whether of plant source or otherwise, which can function in a plant, i.e., which can control or regulate the transcription of a structural gene within a plant cell. As used herein, the term "promoter" means a DNA sequence which can control the level of transcription of a downstream DNA sequence which corresponds to a structural gene (encoding region). Plant promoters may be fused to structural genes by cutting and ligating of DNA sequences, together with substitution of specific nucleotide(s) as needed in ways known in the art. The following plant promoters, preferred for use in regulating chitinase DNA in plants, have been fused to chitinase DNA and introduced into plants resulting in chitinase production by the plants, in accordance with the invention: nopaline synthase promoter (from *Agrobacterium tumefaciens*) chlorophyll a/b binding protein promoter; ribulose bisphosphate carboxylase small subunit promoter; and cauliflower mosaic virus 35S promoter.

Plants transformed with chitinase DNA may be characterized or subjected to assays in various ways. The presence of messenger RNA corresponding to chitinase DNA may be assayed in known ways (e.g., Northern hybridization, primer extension assay) as a measure of transcription of the introduced DNA. The presence of chitinase protein may be assayed in known ways (e.g., SDS-PAGE) as a measure of translation. Chitinase produced by the plant may be assayed for chemical activity by measuring the capacity of chitinase produced by the plant to hydrolyze chitin The biological activity of the chitinase may be assayed by various bioassays which can be used to determine the effect of chitinase produced by the plant on chitinous plant pathogens. One such bioassay is described in Example 4(f).

EXAMPLES

1. Introduction of Chitinase DNA into *E. Coli*.

The overall procedure was to construct a set of random cosmid clones from the *Serratia marcescens* genome which would cover the entire genome several times over in such a way that statistically there was at least a 99% chance of covering every DNA sequence in the genome. Clones carrying an entire chitinase gene were inserted in *E. coli*, which is quite closely related, taxonomically, to *S. marcescens*. The work involved in isolating clones which carry chitinase DNA had the following steps, as explained in detail below.

a) Isolating total *S. marcescens* DNA.
b) Partial digesting of *S. marcescens* DNA.
c) Purifying a fraction of the partial DNA digest in which the DNA fragment size was 22 kb–32 kb.
d) Ligating the purified DNA to a cosmid cloning vector.
e) In vitro packaging into lambda phage.
f) Transfecting *E. coli* cells with lambda phage and selection.
g) Carrying out small scale plasmid isolations on tetracycline resistant colonies and digesting to check that foreign DNA had been cloned.
h) Plating and screening for colonies which clear chitin.
i) Characterizing cosmid clones conferring chitinase activity.

(a) Isolation of total *S. marcescens* DNA

Cells of *Serratia marcescens* QMB1466 were removed from culture storage and streaked on agar media to form single isolated pure colonies.

A single colony was inoculated into 5 mls of 1-bactotryptone, 0.5% yeast extract and 0.5% NaCl (hereinafter LB) liquid medium and grown overnight with shaking at 28° C. One ml aliquots were spun down in 1.5 ml Eppendorf tubes and resuspended in 0.3 ml 20 mM Tris, 10 mM EDTA (pH 8.0). 0.1 ml of 5% SARKOSYL and 0.1 ml of 5 mg/ml pronase were added and the cells were incubated at 37° C. for lysis to proceed for two hours. After this incubation, the solution was passed through a 19 gauge needle to shear the DNA slightly and thus to reduce the viscosity of the solution. Next, 0.5 ml of phenol (pH adjusted to 8.0 with Tris) was added and the mixture shaken in the Eppendorf tube prior to centrifugation. This step was repeated three times, with the supernatant from one centrifugation being re-extracted with fresh phenol. Then the supernatant was extracted three times with 0.8 ml of a one-to-one mixture of phenol and chloroform/isoamyl alcohol (24:1) and once with 0.8 ml of chloroform/isoamyl alcohol. The supernatant from this final spin was brought to 0.3M sodium acetate and the DNA precipitated by addition of 2.5 volumes of ethanol. After centrifugation to pellet the DNA precipitate, the DNA was redissolved in 0.1 ml of 10 mM Tris/1 mM EDTA (hereinafter TE) An aliquot was taken and diluted into 0.5 ml for measurement of the optical density at 260 nm in order to find out the concentration of nucleic acid. Typically this procedure permitted the isolation' of 100–200 micrograms of DNA.

(b) Partial digestion of isolated DNA

The procedure adopted for establishment of appropriate DNA to enzyme ratios for correct partial digestion was the widely used method described in Maniatis pp. 282–283. The objective was to establish conditions where the maximum fluorescence of the partial digestion products occurred in the size range 40–50 kb. 10 ug (microgram) of DNA was incubated in 150 ul (microliter) of the restriction enzyme buffer specified by the manufacturer (New England Biolabs) and dispensed in 15 ul aliquots except for one tube which contained a 30 ul aliquot. 10 units of EcoRl were added to the 30 ul aliquot, the contents of the tube were mixed and a 15 ul aliquot withdrawn, added to the next tube and the contents mixed, and the procedure repeated down the series of tubes. After a one hour incubation at 37° C. the reaction was terminated with 3 ul of 0.25M EDTA/50% glycerol/0.01% bromophenol blue, and the digestion products run on a 0.4% agarose gel which was stained with 0.5 ug/ml ethidium bromide and examined by fluorescence in short wave uv light. The migration of the partial digestion products in the gel was compared to size markers of known size. once conditions were established for partial digestion of chromosomal DNA to the appropriate degree, 200 ug of DNA was digested to this degree in an appropriately scaled-up volume. Partial digests giving weight average sizes at the maximum fluorescence position of 40 kb and 20 kb were mixed and fractionated on a glycerol gradient.

(c) Fractionation of partial digestion products by differential sedimentation

The digestion was terminated by addition of enough 0.5M EDTA to bring the final EDTA concentration to 10 mM followed by incubation of the reaction at 65° C. for 10 minutes, and then was kept on ice until the gradient was loaded. An aliquot was checked for the degree of digestion being appropriate by running on a 0.3% agarose gel with DNA fragment size markers of appropriate size (e.g., digests of lambda DNA).

Linear gradients of 10–40% glycerol were prepared in 38 ml polyallomer tubes. The 10% or 40% glycerol stock solutions were made up in 1M sodium acetate, 5 mM EDTA. 0.5–1.5 ml aliquots of partial digests containing 100–300 ug of partial digest were loaded on top of the gradients which were then spun at 25000 rpm for 16 hours.

At the end of the centrifugation the tubes were punctured at the bottom, 1 ml aliquots were dripped out and the DNA in them analyzed by agarose gel electrophoresis in 0.3% gels. Fractions containing DNA in the size range 22-32 kb were chosen for further work.

Fractions of this size range were pooled and dialyzed against 10 mM Tris 1, mM EDTA (pH 8.0) for 24 hours with three buffer changes.

These fractions were then concentrated by isobutanol extraction (Maniatis, p. 463) to about 0.3 ml, brought to 0.3M sodium acetate and the DNA was precipitated by addition of 2.5 volumes of ethanol. The precipitated DNA was redissolved in 10 ul of TE and the quantity of DNA recovered estimated by measuring the optical density at 260 nm of a dilution of an aliquot of this DNA.

(d) Ligation of size-fractionated DNA to vector DNA

The vector used for cloning the Serratia DNA was pLAFR1. As described by A. Friedman et al., "Construction of a broad host range cosmid cloning vector and its use in the genetic analysis of *Rhizobium meliloti*", Gene, 18, 289-96 (1982), pLAFR1 RI site, a cos site from lambda phage for in vitro packaging, and a tetracycline resistance marker. The vector pLAFR1 selects DNA inserts of about 22 to about 32 kb in length. The vector can be mobilized to other genera of bacteria where it can replicate.

5 ug of pLAFR1 DNA was digested to completion with EcoR1, and the DNA phenol extracted and ethanol precipitated. The precipitated DNA was redissolved in 20 ul of TE.

Test ligations were carried out on both the pLAFR1 DNA and the size-fractionated DNA which was to be cloned to verify that the ends were ligatable.

In a typical ligation of pLAFR1 DNA to size-fractionated Serratia DNA, a 5-fold molar excess of Serratia DNA was adopted. A typical ligation contained in 10 ul 0.4 ug of pLAFR1 DNA and 3 ug of Serratia DNA. The reaction was 66 mM Tris (pH 7.5), 10 mM MgCl2, I mM ATP, 15 mM dithiothreitol, 0.05% BSA, 0.5 mM spermidine and 20 units/ul T4 DNA ligase (New England Biolabs) The reaction was carried out overnight at 15° C.

(e) In vitro packaging of ligation products into lambda phage, particles

Packaging extracts were prepared as described in Maniatis p. 264-267. Freeze thaw lysate was frozen at −80° C. in 10 ul aliquots, and sonic extract was frozen away in IS ul aliquots. One tube of each was thawed on ice and the freeze thaw was added to the sonic extract and mixed gently. Then 5 ul of the ligation was added to the mixture and after gentle mixing, the packaging reaction was allowed to proceed at 25° C. for one hour. The reaction was diluted with 500 ul of 10 mM MgCl2 10 mM Tris (pH 7.5), 10 mM NaCl (hereinafter SM), and 500 ul chloroform were added. The mixture was inverted five times in the capped Eppendorf tube and spun for five minutes in an Eppendorf bench centrifuge.

(f) Transfection of *E. coli* cells with packaged cosmid clones

*E. coli* strain DH1 (ATCC #33849) displays no detectable chitinase activity (see Table II) The strain was grown to saturation in LB containing 0.4% maltose. A 0.2 ml aliquot was withdrawn and mixed with 0.1 ml of SM and 10 ul of the diluted packaging mix. After mixing gently, phage absorption was allowed to proceed for 20 minutes at 37° C.

The transfection was added to 1.7 ml of LB in a tube and the cells permitted to grow out for 40 minutes at 37° C . In the first experiment 20, 100, 500, and 1100 ul aliquots were plated on LB plates containing 1.5% agar and 10 mg/l tetracycline to investigate the colony forming units derived from the packaging. The plates were incubated at 37° C. for 16-20 hours. In a typical experiment a 10 ul aliquot of packaging dilution would contain 1000 colony forming units.

(g) Small scale plasmid preps to investigate the quality of the bank

Single tetracycline resistant colonies were picked from plates at the end of stage (f) above into 8 ml aliquots of LB containing 0.5 g/l uridine and incubated with aeration for 12-20 hours at 37° C. Cells were spun down and resuspended in 0.2 ml 50 mM glucose, 20 mM Tris, 10 mM EDTA (pH 8.0). The cells were then lysed in 0.4 ml 0.2M NaOH, 1% SDS. This was neutralized with 0.3 ml 3M potassium acetate which had been brought to pH 5.0 with acetic acid and incubated on ice for five minutes. After thorough mixing, the mixture was spun at 8000 rpm for ten minutes. The supernatant was precipitated with 0.6 volumes of isopropanol and the DNA recovered by centrifugation in a bench top Eppendorf centrifuge The pelleted DNA was redissolved in 0.3 ml TE and extracted with equal volumes of phenol and chloroform. After centrifugation the supernatant was brought to 0.3M sodium acetate and the DNA precipitated with 2.5 volumes of ethanol After centrifugation the DNA was redissolved in 0.05 ml of TE and 5 ul aliquots were used for restriction enzyme digestion followed by gel electrophoresis.

In a typical experiment eight independent clones were grown up and 50% of them contained inserts.

(h) Direct plating on chitin-containing medium for a screen for chitinase activity Theoretically about 500 independent clones of a genome the size of *E. coli* should give a 99% chance of getting any particular sequence among the clones. It is desirable to independently isolate any clone with chitinase activity at least once. Five thousand colonies were plated out at about 250 colonies per plate on LB medium containing 2.0% colloidal chitin and 10 mg/l tetracycline. This concentration of chitin had been previously shown to clearly evidence the chitinase activity of *S. marcescens* QMB1466.

After about seven days at 32° C., certain colonies gave rise to clear zones around them. Altogether about twenty different colonies gave rise to convincing clear zones in their vicinity. See Table II and step (i) below. In Table II, DH1 is the original *E. coli* (step f); DH1/pLAFR1 is *E. coli* DH1 containing the cosmid vector pLAFR1 but without insert; DH1/C3 is *E. coli* DH1 containing cosmid vector pLAFR1 with one chitinase size class insert; and DH1/C1 is *E. coli* DH1 containing cosmid vector pLAFR1 with a second chitinase size class insert (this strain has been deposited with the American Type Culture Collection in Rockville, Maryland as ATCC No. 67152).

(i) Characterization of cosmid clones conferring chitinase activity

Ten of the twenty colonies were inoculated into 8 ml of LB tet medium and plasmid DNA prepared as above. This DNA was analyzed for the DNA sequences in the plasmid by digestion with EcoR1. Each of the ten plasmid DNAs fell into one of two distinct size classes after EcoR1 digestion. Seven out of the ten cosmid clones showed one large EcoR1 fragment of about 25 kb, in addition to the vector band of 21.6 kb. Of these, one (C3) was chosen for further characterization (see Table II and associated text) Three of the plasmids showed insert fragments of 3 kb, 9.5 kb and 17 kb, in addition to the vector band of 21.6 kb. Of these, one (C12) was chosen for further characterization (see Table II and associated text).

The phenotype of chitinase production was shown to be plasmid borne by reintroduction of the plasmid into E. coli bacteria by transformation of the bacteria with plasmid DNA. 1 ul out of the 50 ul of plasmid DNA prepared as in (h) was incubated with 0.1 ml of competent E. coli cells prepared essentially by the method of M. Dagert and S. D. Ehrlich, Gene, 6, 23–28 (1979). After a 20 minute incubation on ice and a two minute heat shock at 37° C., bacteria were grown out in LB medium for one hour and plated on LB tetracycline chitin plates. Bacteria which acquired tetracycline resistance all acquired the capacity to make chitinase.

The above experiments provide evidence that S. marcescens QMB1466 contains two independent chitinase genes which have been isolated on distinct cosmid clones. The means is therefore presented to express these genes either together or separately in a recipient organism.

2. Introduction of chitinase DNA into Pseudomonas species.

(a) Isolation of Pseudomonas species from the rizosphere

Pseudomonas fluorescens strain NZ130 and Pseudomonas nutida strain MK280 were isolated from radish roots, and soybean roots, respectively, by plating on King's Medium B from serial dilutions of root washings. See in general T. Suslow, "Role of Root-Colonizing Bacteria in Plant Growth," Phytopathogenic Prokaryates, Vol. I, M. S. Mount and G. H. Lacy eds , 187–223 (1982) for details of fluorescent pseudomonas isolation and characterization for colonizing ability and plant growth promotion. Strain NZ130 has been identified as P. fluorescens Biotype D (Pseudomonas chlororaphis in some taxonomies) and strain MK280 as P. putida. Their characteristics include the following:

TABLE I

|  | NZ130 | MK280 |
| --- | --- | --- |
| Fluorescent on King's Medium B | + | + |
| Fluorescent on King's Medium A | − | − |
| Pyocyanine Production | − | − |
| Oxidase | + | + |
| Lecithinase | + | − |
| Gelatin Hydrolysis | + | − |
| Arginine Dihydrolase | + | + |
| Growth at 4° C. | + | − |
| Growth at 37° C. | − | + |
| Growth at 41° C. | − | − |
| Green Phenazine Pigment | + | − |
| Motility | + | + |
| Inhibition of Erwinia sp. | + | + |
| Inhibition of Pythium sp. | + | − |
| Clones resistant to rifampicin (100 ug/ml) | + | + |

Strain NZ130 has plant growth promoting characteristics on a number of crops including potato, radish, soybean, cotton, and sugar beet. Strain NZ130 also has biological control characteristics with respect to Pythium sp., but no measurable chitinase activity. Root colonization data collected for NZ130, in general, reach average population densities of $5.5 \times 10^4$ colony-forming units (cfu) per mg root tissue (dry weight) on radish, soybean and cotton.

Strain MK280 has been shown to increase the emergence of soybean and to effectively colonize roots of soybean and sugar beets. Population densities, in general reach as high as $1.2 \times 10^6$ cfu/mg root tissue.

(b) Mobilization of cosmid clones into Pseudomonas species pLAFR1 is a mobilizable cloning vector derived from pRK290 (Ditta) It can be mobilized into other genera of bacteria using a helper plasmid pRK2013 in a three-way mating process. Two Pseudomonas strains were chosen as recipients for these matings; these were NZ130r (NZ130, rifampicin resistant) and MK280r (MK280, rifampicin resistant). The donor (transferor) strain was E. coli DH1 or HB101 containing one of the two chitinase cosmid clones, and the helper strain was HB101 containing pRK2013, all of which materials are commonly available.

Donor, recipient and helper strains were grown up to mid-log phase, without selection, in LB. 0.05 ml aliquots from each strain were added to each other and the mixture put out as a 0.15 ml aliquot on an LB plate for 12–16 hours at room temperature. After the conjugation, a loop was run through the cells. Cells from the loop were resuspended in 10 mM MgSO4, and the mixture of cells plated at various dilutions on minimal sucrose tetracycline (10 mg/l) plates.

This procedure selected against E. coli, which cannot grow on minimal sucrose plates, and selects for Pseudomonas cells which acquire the tetracycline resistance gene. Exconjugant cells were obtained and were tested for chitinase activity as above. See Table II. In Table II, TS031 is NZ130r with cosmid vector pLAFR1 but without insert; TS043 is NZ130r with cosmid vector pLAFR1 with one chitinase size class insert (corresponding to the insert of DH1/C12 present in ATCC No. 67152) TS035 is MK280r with cosmid vector pLAFR1 but without insert; and TS044 is MK280r with cosmid vector pLAFR1 with one chitinase size class insert (corresponding to the insert of DH1/C3). TS044 has been deposited with the American Type Culture Collection in Rockville, Md. (ATCC No. 39637). Note that Table II also lists data for two naturally occurring, chitinase-producing strains which are not root colonizers: Serratia marcescens strain ATCC 990 and a strain of naturally occurring Arthrobacter sp.

TABLE II

| | Efficiency of Chitin Hydrolysis by Chitinase-Producing Bacteria* Growth Temperature | | | | |
| --- | --- | --- | --- | --- | --- |
| STRAIN | 21° C. | 25° C. | 28° C. | 32° C. | 37° C. |
| Serratia marcescens | | | | | |
| ATCC 990 | 1.28 | 1.51 | 2.17 | 2.22 | 1.41 |
| Arthrobacter sp. | | | | | |
| TS037 | 1.0 | 1.06 | 1.07 | 2.0 | 1.0 |
| E. coli | | | | | |
| DH1 | 1.0 | 1.0 | 1.0 | 1.0 | 1.0 |
| DH1/pLAFR1 | 1.0 | 1.0 | 1.0 | 1.0 | 1.0 |
| DH1/C3 | 1.12 | 1.12 | 1.12 | 1.13 | 1.13 |
| DH1/C1 | 2.12 | 1.12 | 1.12 | 1.32 | 1.82 |
| P. fluorescens | | | | | |
| TS031 | 1.0 | 1.0 | 1.0 | 1.0 | 1.0 |
| TS043 | 1.10 | 1.10 | 1.10 | 1.28 | 1.14 |
| P. putida | | | | | |
| TS035 | 1.0 | 1.0 | 1.0 | 1.0 | 1.0 |
| TS044 | 1.12 | 1.06 | 1.06 | 1.14 | 1.15 |

*Efficiency reported as the ratio of clearing zone diameter in LB agar amended with 2.0% colloidal chitin to colony diameter. A value of 1.0 represents no clearing detectable.

3. Introduction of Chitinase DNA in Tobacco Under Control of a Nopaline Synthase Promoter.

(a) Plant transformation.

The coding region of the chitinase gene in the C12 chitinase size class insert (described in Example 2 above) was determined by nucleotide sequence analysis of the DNA (this coding region referred to herein as the chiA gene). The sequence of the chitinase A gene is presented in FIG. 1. Comparison of the N-terminal sequence with signal sequences of other prokaryotes (See, for example, Inouye et al. (1983), *Science*, 221, 59–61) reveals the putative chitinase signal peptide. As can be seen, the eighth through eighteenth amino acids are hydrophobic and the predicted cleavage site is between the alanines at the 23 and 24 positions. See, J. Jones et al., *EMBO J.*, 463–473 (1986) regarding sequence information and G. Van Heijne *EMBO J.*, 3, 2315–2318 (1984) regarding signal peptide sequences, both of which are incorporated herein by reference. This nucleotide sequence information was used in the creation of constructions which led to the expression of the bacterial chitinase gene in plant cells. Sequence information of use in practicing the invention is set forth in the paragraphs below.

These constructions required the modification of nucleotide sequences at the 5' end of the chitinase gene. This was carried out in several steps. An NdeI site (CATATG) was introduced at the N-terminal methionine-encoding ATG of the chiA gene by oligonucleotide site-directed mutagenesis; M. J. Zoller et al., *Nucleic Acid Res.*, 10, 6487–6500 (1985). Sequence information is given below.

| | |
|---|---|
| chiA wild type sequence | GGAATCAGTT ATGCGC |
| chiA wild type sequence | GGAATCAGTT ATGCGC |
| chiA mutated sequence | GGAATCACAT ATGCGC (gives an NdeI site at the ATG) |

The chiA gene was cut with NdeI and fused to a DNA fragment carrying the Agrobacterium nopaline synthase (nos) promoter which had also been modified in a similar manner to yield an NdeI site at the ATG. The nopaline n synthase gene has been characterized; Depicker et al., *J. Mol. Appl. Genet.*, 1, 561–573 (1982). Using these two constructions, the chiA gene was litigated directly to the nos promoter. Sequence information is shown below.

| | |
|---|---|
| nos-chiA fusion | TCTGCAT ATGCGCAAA |

Modifications of the resulting fusion were made using site-directed mutagenesis in order to improve the translation signals. Sequence information is shown below.

| | |
|---|---|
| modified nos/chiA fusion #1 | TCTGAAT ATGCGCAAA |
| modified nos-chiA fusion #2 | TCTGAAT ATGGCCAAA |

Each of these constructions was set up with a nos gene fragment carrying signals for polyadenylation placed at an EcoRV site 25 bp past the TAA. These constructions were introduced into plant cells using Agrobacterium by ligating them into binary vectors, P. van den Elzen et al., *Plant Molecular Biology*, 5, 149–154 (1985) and mobilizing the resulting constructions into the Agrobacterium strain LBA4404, A. Hoekema et al., *Nature*, 303, 179–180 (1983).

These strains were then used in cocultivation experiments with tobacco cells, and calli which grew on kanamycin were selected.

(b) Assays

Large numbers of independent calli (approximately 400) prepared as described above were harvested approximately six weeks after initiating the selection regime and were analyzed for the expression of mRNA homologous to the bacterial chitinase gene and for protein which was antigenic to an antibody raised against the bacterial chitinase protein. This antibody was prepared using a protein sample in which the chitinase band had been eluted from a preparative acrylamide gel and injected into rabbits to elicit antibodies to the protein in the rabbit serum. J. Jones et al., *EMBO J.*, 5, 467–473 (1986).

The results of these experiments can be summarized as follows:

(i) Chimeric nos-chitinase mRNA was detected in the transformed plant cells. About two-fold more mRNA was detected in modification #2 than in modification #1 or in the original CATATG construction.

(ii) Bacterial chitinase protein was detected in the plant cells. The modified nos-chiA fusion #2 gave rise to about four-fold more protein on a per total protein basis than modification #1 and eight-fold more than the original NdeI site fusion.

In short, these results showed the expression of chitinase protein in plant cells in detectable quantities.

4. Introduction of Chitinase DNA in Tobacco Under Control of a Chlorophyll A/B Binding Protein Promoter (CAB Promoter) or a Ribulose Bisphosphate Carboxylase Small Subunit Promoter (SSU Promoter).

(a) Preparation of CAB constructs

The modified nos-chiA fusion #2 of Example 3 generated a BalI restriction site (TGGCCA) immediately downstream of the ATG. This was used to form a fusion with a chlorophyll a/b binding protein gene (CAB 22L) octopine synthase fusion which also contained a BalI restriction site in a corresponding position relative to the ATG. See P. Dunsmuir et al., *Nucleic Acid Res.*, 13, 2503–2518 (1985). This construction had the DNA sequence shown below.

| | |
|---|---|
| CAB 22L/ ocs | AAACC ATGGCCAGATCCCGGG |

DNA carrying this construction was cut with BalI and ligated to BAlI cut nos/chiA modification #2 in such a way that the nos 3' polyadenylation signals were retained 3' to the chiA gene. The resulting construction had a sequence around the ATG as shown below.

| | |
|---|---|
| CAB-chiA fusion | AAACC ATGGCCAAA |

(b) Preparation of SSU constructs

The resulting CAB-chiA fusion described above retained an NcoI (CCATGG) site at the ATG. This was used to fuse the chiA coding region to the 5' end of an expression cassette which used 5' and 3' sequences from a gene highly expressed in the petunia leaf, namely SSU gene #301; see C. Dean et al., *EMBO J.*, 4, 3055–3061, (1985). This expression cassette (pAGS007) contains a coding sequence flanked by an NcoI site at the ATG and a BGlII (AGATCT) BamHI (GGATCC) or BclI (TGATCA) site close to and 3' to the termination codon to be placed between SSU301 5' and 3' sequences. The expression cassette is deposited within E. coli JM83-AMB007 (ATCC 67125); see U.S. patent application Ser. No. 883,604, which is incorporated by reference. Fusion to the SSU cassette creates a novel sequence in the vicinity of the chitinase ATG. Sequence information is given below.

| SSU-chiA fusion | TAACC ATGGCCAAA |

During the construction of the nos-chiA fusion the chiA coding region fused to the nos 5' sequences was cloned as a BamHI (Klenow treated) to EcoRV (partial digestion) fragment into the SmaI site of a pUC vector containing a TaqI fragment which encodes the nos 3' region. The EcoRV site used was 25 ebp downstream of the chiA translation termination codon. This fusion therefore added the nos 3' region onto the 3' end of the chiA coding region, completing the nos-chiA fusion. The resulting plasmid had a BamHI site (from the pUC linker) at the junction of the chiA and nos 3' sequences. This BamHI site was used to fuse the 3' flanking sequences of the SSU expression cassette to the chiA coding sequence (a BamHI site can fuse to a BglII site).

(c) Plant transformation

The CAB and SSU constructions were cloned into the BamHI site of binary vector pAGS135 which is very similar to pAGS112 described in P. van den Elzen et al., Plant Molec. Bio., 5, 149-154. (1985). The difference is that the unique XhoI site in pAGS112 has been removed by Klenow+dNTP treatment of the linearized DNA and religation. The resulting constructions were mobilized into Agrobacterium strain LBA4404. A. Hoekema et al., Nature, 303, 179-180 (1983).

The resultant Agrobacterium strains were cocultivated with protoplasts isolated from N. tabacum. P. van den Elzen et al., Plant Molec. Bio., 5, 149-154 (1985). Transformed plant material was selected for its ability to grow on 50 mg/l kanamycin, then regenerated.

The transgenic tobacco plants were transferred to the greenhouse once they had established a sufficient root system. They were assayed for expression of chitinase RNA and chitinase protein three weeks after they had been in the greenhouse (previously established to be the time of maximal CAB and SSU RNA levels).

(d) Assay for chitinase protein

The level of chitinase protein was assayed by a Western blot analysis in which an antibody probe was used to detect chitinase protein on a nitrocellulose filter carrying the size-fractionated polypeptides. The amount of chitinase protein was evaluated using a standard dilution series of chitinase protein isolated from bacterial strains which abundantly express the chitinase. These experiments showed that in the most abundantly expressing SSU-chitinase transformants, the bacterial chitinase protein accumulated to 0.1-0.2% of total leaf protein. Of fifteen plants assayed, seven gave rise to greater than or equal to 0.1% of total protein as chitinase. For the CAB-chitinase transformant, one gave rise to a protein level of 0.1% chitinase, and on average these constructions gave rise to 2-4 fold less chitinase protein than was found in the SSU-chitinase transformants.

(e) Assay for chitinase mRNA

The levels of chitihase RNA were assayed by primer extension. In this assay an oligonucleotide specific to the chitinase RNA was annealed to total PNA and then extended in a reverse transcriptase reaction back to the 5' end of the message. The amount of extended fragment then gave a measure of the levels of chitinase RNA in the total RNA. The results correlated broadly with the levels of chitinase protein observed in the individual transformants A comparison of the chitinase RNA levels from plants transformed with noschiA, CAB-chiA and SSU-chiA showed that the highest expressing SSU-chiA construct transformant gave rise to about 15× more chitinase mRHA than the best CAB-chitinase constructs and at least 200× more mRNA than the nos-chitinase constructs.

(f) Assay for chitinase biological activity

Biological activity of chitinase produced by transformants was assessed in a bioassay using, as a model disease, Tobacco Brown Spot caused by Alternaria alternata and Alternaria lonaipes. The pathogen infects leaves causing discrete, readily quantified lesions and is of a class of fungi, Fungi Imperfecti, having cell walls containing chitin.

Leaf disks, 9.0 cm in diameter, were cut from the center of tobacco leaves taken from acropetal positions 4-10 as described by H. Spurr, Tobacco Science, 17, 145-148 (1973). plants utilized were either transformed with a CAB: chiA fusion, 1771.2, or were transformed but did not contain chiA, SBT2.9. The parental tobacco plant, Wis38, had previously been tested for susceptibility to Brown Spot and ATCC strain 26293 of A. lonaipes was most virulent. Conidial suspensions were prepared as described (H. Spurr, Tobacco Science, 17, 145-148, 1973), and adjusted to approximately $\log_{10}$ 5.0 conidia ml$^{-1}$ in a chamber haemocytometer. Twelve drops (each of 10 ul) of conidial suspension were placed in a uniform pattern on the underside of each of seven leaf disks per treatment. Leaf disks were incubated in a Conviron Seed Germinator with settings at 21° C., 95% RH, and 8 hour low intensity fluorescent light photoperiod.

After eight days, leaf disks were observed for comparative disease development. Total necrotic lesions were counted and the lesion diameter measured with a metric caliper. Diameter values given (Table III) are inclusive only of the brown necrotic tissue and not the chlorotic halo associated with the whole infection. Leaf disks from identical leaf positions were most directly comparable as differences in susceptibility with leaf age were known.

Wis38 plants containing and expressing chiA had fewer total Brown Spot lesions, fewer lesions per disk, and necrotic areas which did develop were of generally lesser diameter than plants not transformed with chiA.

TABLE III

| Plant | Total Lesions | Lesions/ disk | Diam.$^a$/Total | Diam.$^b$/Leaf |
|---|---|---|---|---|
| 1771.2 | 10 | 1.7 | 0.2 | 1.1 |
| SBT2.9 | 23 | 3.3 | 0.6 | 1.5 |

$^a$Mean diameter of necrotic lesions for all inoculated spots.
$^b$Mean diameter of necrotic lesions for most susceptible leaf pairs.

In another series of readings, three other transformants (1781.1, 1781.5, 1781.4) prepared as above, were compared with a control (Wis38). The results, shown in Table IV below, again show the positive effect of chitinase, produced by the transformed plant, on disease resistance. Each of the three transformants showed, relative to the control, decreased infection ratio and decreased lesion sizes.

TABLE IV

| Plant | Relative level of chiA | x̄ infection ratio (%)[a] | X diam./ X diam./lesion/ disk (mm)[b] | lesion (mm)[c] |
|---|---|---|---|---|
| Wis38 | 0 | 82 | 6.4 ± 0.4 | 6.4 ± 0.20 |
| 1781.1 | 1X | 43 | 6.1 ± 0.5 | 6.2 ± 0.33 |
| 1781.5 | 5X | 62 | 5.6 ± 0.8 | 6.3 ± 0.38 |
| 1781.4 | 20X | 55 | 4.8 ± 0.4 | 4.6 ± 0.33 |

[a] Mean percent infection (infections/total inoculation points X100) per replication.
[b] Mean infection lesion (necrotic area) diameter per leaf disk replication.
[c] Mean infection diameter normalized per necrotic lesion.

5. Secretion of the cecropin peptide after fusion to the chiA signal sequence.

The signal sequence from the chiA gene (FIG. 1; nucleotides 1-69) was used to direct the secretion of a heterologous protein (cecropin) in plant cells. The gene which encodes cecropin A (Bowman H. G. et al., *Ann. Rev. Microbiol.*, 41, 103-126, 1987, which is incorporated herein by reference) was prepared by oligonucleotide synthesis (Zoller et al., *Nucl Acid Res.*, 10, 6487-6500, 1987, which is incorporated herein by reference). Two complementary DNA sequences, each of 122 nucleotides, were synthesized, then annealed together to from the fragment shown in FIG. 2 which encodes the mature cecropin A peptide flanked by SalI and BglII restriction sites at the 5' and 3' ends of the gene coding region. This synthetic gene was first ligated into the plasmid pUCI18 to form the plasmid pUCI18cecMP (Vieira J. et al., *Methods in Enzymology*, 152, 3-11, 1987, which is incorporated herein by reference).

The plasmid pCHIT503 contains the *Serratia marcescens* chiA gene coding region fused to the cauliflower mosaic virus 35S promoter, and the nopaline synthase polyadenylation region. The plasmid was derived from pJJ2104 (Lund, P. et al., *Plant Physiol.*, 91, 130-135, 1989, which is incorporated herein by reference) by the introduction, using oligonucleotide site-directed mutagenesis (Zoller et al., *Nucl. Acid Res.*, 10, 6487-6500, 1987, which is incorporated herein by reference), of a SmaI site at nucleotide 78 in the chiA coding region (FIG. 1).

In order to express a form of cecropin A peptide that was secreted into the intercellular space in transgenic plant tissue, the first step was to fuse the cecropin gene to the chiA gene. The plasmid pCHIT503 was cleaved with SalI, which cuts at nucleotide 528 in the chiA coding region, and XbaI which cleaves between the chiA coding region and the nos polyadenylation sequence, as shown in FIG. 3. In parallel, the cecropin A coding region was excised from pUCI18cecMP by cleavage with SalI and SmaI, and this fragment was ligated into the plasmid pCHIT503, forming a fusion protein between a truncated chiA coding region (nucleotides 1-528) and the cecropin A coding region. The next step was to form a perfect fusion between the chiA signal sequence (nucleotides 1-69) and the cecropin A gene. This was achieved by oligonucleotide based loop-out mutagenesis of nucleotides 70-528 in the chiA gene, resulting in the gene specified in FIG. 4. M. Eghtedarzadeh et al., *Nucl. Acid Res.*, 14, 5115, 1986, which is incorporated herein by reference.

The plasmid carrying the fusion of cecropin A to the chiA signal sequence and the CaMV 35S promoter is called CEC3 (FIG. 3). The EcoRI-HindIII fragment from the CEC3 plasmid, containing the chiA:cecropin gene, was cloned into the binary plasmid pAGS502. Plasmid pAGS502 is a derivative of pAGS112 (P.van den Elzen et al., *Plant Mol. Biol.*, 5, 149-154, 1985, which is incorporated herein by reference) which is altered by the introduction at the BamHI sites of a polylinker region containing HindIII, EcoRI, XhoI, XbaI and BamHI sites. The resulting plasmid was mobilized into Agrobacterium strain LBA4404 (A. Hoekema et al., *Nature* 303, 179-180, 1983, which is incorporated herein by reference). Tobacco SRI leaf disc transformation and regeneration were carried out according to R. Horsch et al., *Science*, 227, 1229-1231, 1985, which is incorporated herein by reference.

Multiple independent transformed tobacco plants were generated which carried the cecropin A coding region fused to the chiA signal peptide coding region. In parallel, transformants were generated which carried the cecropin A coding region fused, without a signal sequence, to the plant SSU301 promoter (Dean et al., *Proc. Natl. Acad. Sci. USA*, 82, 4964-4968 1985 which is incorporated herein by reference). In order to determine the location of the cecropin peptide in the transgenic tobacco tissues, protein preparations were made from (i) total leaf tissue, and (ii) the extracellular spaces in leaf tissue. The level of cecropin protein was then measured in theses samples in a standard ELISA (using horse radish peroxidase) by reaction with a polyclonal antibody raised in rabbits against synthetic cecropin A peptide (E. Harlow et al., Cold Spring Harbor: Antibodies, A Laboratory Manual, pp. 553-612 1988 which is incorporated herein by reference). A comparison of the amount of protein measured in the extracellular space and in total leaf extracts provides an estimate of the level of secretion of cecropin protein. These results are summarized in Table V. Four independent transformants which carry the chiA:cecropin fusion gene were compared with two independent transformants which carried the gene for the cecropin A peptide without an attached signal sequence. These data indicate that when cecropin is fused to the chiA signal sequence, cecropin is found primarily in the extracellular fraction, while in the absence of a signal sequence cecropin is found mainly within the cell.

TABLE V

| Transformant | Cecropin Level (ng) | | Enrichment |
|---|---|---|---|
| | Total Soluble | Extra Cellular | |
| a) chiA: cec | | | |
| 3-4 | 0.23 | 2.6 | 10 |
| 3-7 | 0.07 | 0.14 | 2 |
| 3-8 | 0.07 | 0.2 | 3 |
| 3-9 | 0.01 | 0.5 | 50 |
| b) cec | | | |
| 6-8 | 0.09 | 0.12 | 1.3 |
| 6-1 | 0.43 | 0.08 | 0.2 |
| 6-11 | 0.79 | 0.98 | 1.2 |

What is claimed is:

1. A method of inhibiting chitinous fungal plant pathogens comprising introducing into a plant a DNA sequence encoding for chitinase activity to create a transformed plant under conditions whereby the transformed plant expresses chitinase in active form.

2. The method of claim 1 wherein said DNA sequence is isolated from a bacterial source.

3. The method of claim 1 wherein said DNA sequence has the sequence of chitinase-encoding DNA contained in ATCC #39637 or ATCC #67152.

4. The method of claim 1 wherein said DNA sequence is fused to a plant promoter.

5. The method of claim 1 wherein said DNA sequence is introduced using Agrobacterium.

6. The method of claim 1 wherein the transformed plant expresses chitinase in biologically active form as measurable by an assay using Tobacco Brown Spot.

7. A transformed plant resistant to chitinous fungal plant pathogens, said transformed plant containing a DNA sequence encoding for chitinase activity and said DNA sequence having been introduced into the plant by transformation under conditions whereby the transformed plant expresses chitinase in active form.

8. The plant of claim 7 wherein said DNA sequence is isolated from a bacterial source.

9. The plant of claim 7 wherein said DNA sequence has the sequence of chitinase-encoding DNA contained in ATCC #39637 or ATCC #67152.

10. The plant of claim 7 wherein said DNA sequence is fused to a plant promoter.

11. The plant of claim 7 wherein said DNA sequence is introduced using Agrobacterium.

12. The plant of claim 7 wherein the transformed plant expresses chitinase in biologically active form as measurable by an assay using Tobacco Brown Spot.

* * * * *